United States Patent [19]
Rodder

[11] Patent Number: 5,313,955
[45] Date of Patent: May 24, 1994

[54] PULMONARY FLOW HEAD

[76] Inventor: Jerome A. Rodder, 775 Sunshine Dr., Los Altos, Calif. 94022

[21] Appl. No.: 969,796

[22] Filed: Oct. 30, 1992

[51] Int. Cl.⁵ .......................... A61B 5/08; A61B 5/087
[52] U.S. Cl. ................................ 128/725; 128/204.21; 128/204.22; 128/716; 73/861.42; 73/861.52
[58] Field of Search .................... 128/204.21, 204.25, 128/205.24, 204.22, 205.23, 716, 718, 719, 724, 207.14, 725; 73/861.42, 861.52, 861.61, 861.63

[56] References Cited

U.S. PATENT DOCUMENTS

| | | | |
|---|---|---|---|
| 3,735,752 | 5/1973 | Rodder | 128/2.08 |
| 3,949,739 | 4/1976 | Rodder | 128/2.08 |
| 4,259,968 | 4/1981 | Rodder | 128/724 |
| 4,961,344 | 10/1990 | Rodder | 128/725 |

Primary Examiner—William E. Kamm
Assistant Examiner—Brian Green
Attorney, Agent, or Firm—Christie, Parker & Hale

[57] ABSTRACT

A flow head for ventilators includes a tubular open-ended breath transmission passage, and a tubular open-ended inside tube mounted axially inside the breath transmission passage. The inside tube is mounted in the passage by a fixed annular partition, and the ends of the inside tube extend slightly beyond a pair of perpendicular outlet ports on opposite sides of the partition. The inside tube produces a constriction to bi-directional gas flow in the passage which produces a pressure drop across the outlet ports. A pressure sensor connected across the outlet ports measures the pressure drop and therefore produces a measurement of gas flow in the passage. Various sizes of patient gas delivery tubes, endotracheal tubes for ventilator therapy, or tubes for spirometry or anesthesia can be connected to the upstream end of the flow head for producing accurate measurements of gas flow. The inside diameter of the inside tube in the flow head is equal to or slightly less than the inside diameter of the endotracheal tube, within a range progressing from about zero to about one mm less, across a range of endotracheal tube sizes from about 2.5 mm to about 9 mm, which produces a surprisingly smooth gas flow through the flow head and resulting stable pressure drop measurements. The invention also reduces the dead volume within the system by requiring the smallest possible size of breath transmission tube compared to the size of the inside tube. A pressure sensor can be used to measure gas flow as an alternative to a flow rate sensor with a source of bias gas.

10 Claims, 3 Drawing Sheets

PULMONARY FLOW HEAD

FIELD OF THE INVENTION

This invention relates to flow heads for use in measuring gas flow in pulmonary equipment such as ventilators.

BACKGROUND OF THE INVENTION

My U.S. Pat. No. 4,259,968 discloses a flow head for a spirometer having a breath transmission passage with opposite ends open to the atmosphere. A patient breathes through the breath transmission passage bi-directionally. An inside tube having a substantially smaller diameter than the breath transmission passage produces a restriction on air flow between the ends of the passage. Intermediate ports through the wall of the breath transmission passage are located near the restriction, i.e., near the ends of the inside tube where gas velocity is low and thus turbulence is small. Flexible tubing connections to the ports on the breath transmission passage lead to a flow rate sensor controlled by a source of bias gas. The sensor measures a pressure drop in the flow head produced by the bi-directional gas flow from a patient through the breath transmission passage. An external bridge circuit becomes unbalanced in response to the bi-directional flow of gas through the passage and this produces a measurement of gas flow.

In the flow head described in the '968 patent, the patient breathes through flexible tubing coupled to the upstream end of the flow head. Such patient gas delivery tubing can be an endotracheal tube adapted for releasable connection to the end of the breath transmission passage. There are different sizes of patient gas flow tubes depending upon patient breath flow rate. An endotracheal tube for pediatric use, for example, is much smaller in diameter than adult patient sizes. Such a gas flow head is typically used with a gas flow rate sensor using a supply of bias gas to produce accurate flow measurements. This flow head is not easily adaptable to use with a pressure sensor.

Flowmeters are used to measure patient gas volume in spirometry, in ventilators, or in metabolic studies where the amount of calories given to a patient can be determined if an accurate flowmeter is available. A challenging problem is to extend the range of flowmeter accuracy in the low flow area, such as in pediatric uses. Flowmeters could also be used for making critical gas flow measurements in anesthesia.

The flow head should be placed next to the patient's endotracheal tube in order to measure bi-directional gas flow at the patient. Most flowmeters are placed at the exhalation side and, therefore, they do not produce inhalation flow measurements. By knowing both inhalation and exhalation flows, metabolic studies can be performed and the amount of calories (effort) expended by the patient can be calculated. In addition, gas leakage can be calculated.

For pediatric use a patient gas delivery tube of 15 mm diameter or less is commonly used; a 22 mm gas delivery tube is commonly used for adult anesthesia and spirometry. For pediatric use there can be a large amount of dead volume in the flow head. This dead volume should be minimized to inhibit the baby from rebreathing exhaled breath. In one recently introduced monitor the dead volume is 1.4 cc. For an infant who breathes only a 5 cc volume, 1.4 cc is a large volume to rebreathe.

The present invention is based on a recognition that significant improvements in the accuracy of the output from the flow head sensor can be produced by designing the structure of the flow head to match certain sizes of patient breath delivery tubes. Flowmeters accurate in the low flow range for pediatric use can be produced. The invention also results in a less expensive flow head; it minimizes dead volume; and it can be used with a pressure sensor coupled to the flow head for measuring gas flow, which in many instances can be an advantage over a sensor that detects flow and requires a source of bias gas.

SUMMARY OF THE INVENTION

Briefly, one embodiment of this invention provides a flow head for measuring gas flow in a pulmonary system such as a respirator system. A patient gas delivery tube is connected to an upstream end of the flow head. The flow head includes an elongated open-ended tubular breath transmission passage and an elongated open-ended inside tube mounted axially inside the passage to provide a constriction to gas flow in the passage. A pair of axially spaced-apart outlet ports on the side of the breath transmission passage are arranged to produce a pressure drop across the outlet ports in response to constricted gas flow in the passage. A patient gas delivery tube coupled to the upstream end of the breath transmission passage directs the flow of patient gas through the passage. The inside diameter of the inside tube is substantially the same as the inside diameter of the patient gas delivery tube. This has the surprising result of producing a smooth flow of gas through the passage with a stable measured gas pressure drop across the outlet ports of the flow head; whereas very small changes in the diameter of the inside tube compared to the patient gas delivery tube produce poor results. The invention is particularly useful in pediatric size gas delivery tubes ranging in diameter from about 2.5 mm to about 5 mm. In the past where the inside tube of the flow head is greatly larger in diameter than such a pediatric-size gas delivery tube, it was difficult to obtain measurable and stable gas flow measurements. However, with this invention in which the inside tube is substantially the same diameter (or within a tolerance range of plus zero to minus about 12% compared to the diameter of the patient gas delivery tube) surprisingly stable gas flow through the passage and resulting stable measurements of pressure drop across the flow head are produced. These results are obtainable for endotracheal tubes having a range of diameters from about 2.5 mm to about 9.0 mm. Other advantages include minimal noise generated in the output signal, and minimized dead volume within the flow head. These and other aspects of the invention will be more fully understood by referring to the following detailed description and the accompanying drawings.

DETAILED DESCRIPTION

Figure 1:
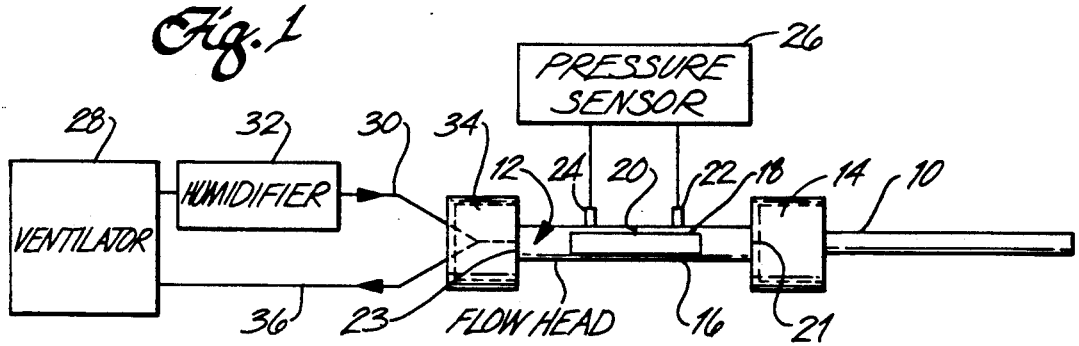
FIG. 1 is a schematic view showing a flow head and endotracheal tube of this invention connected to a ventilator system.

FIG. 1 shows a ventilator system for delivering gas, such as air under pressure, to a patient (not shown). The system is an example of a respirator system in which the present invention can be used. The system includes a gas delivery tube such as an endotracheal tube 10 for patient inhalation from and exhalation to a flow head 12. An adapter 14 connects the endotracheal tube to the upstream end of the flow head. The flow head includes an elongated tubular outer passage 16, also referred to as a breath transmission passage, containing an elongated inside tube 18 of smaller diameter than the tubular outer passage 16. The inside tube 18 and the outer passage 16 are aligned on a common central axis. The inside tube is very thin in wall thickness. An annular partition 20 midway between the upstream and downstream ends of the outer passage 16 extends perpendicularly across the inside diameter of the outer passage to hold the inside tube in a fixed axial position within the outer passage. The partition is a rigid solid piece that diverts gas flow through the tubular open-ended inside tube 18. According to the present invention, the diameter of the inside tube 18 is essentially the same as the diameter of the endotracheal tube 10. This arrangement is described in more detail below.

The thin-walled inside tube 18 acts as a restriction to air flow between the ends of the outer passage 16. The outer passage has a first end 21 and a first intermediate port 22 between its first end 21 and the partition. The outer passage also includes a second end 23 and a second intermediate port 24 between the second end 23 and the partition. The ports 22 and 24 are located between the ends of the inside tube and the partition. When a patient exhales into the first end 21 of the breath transmission tube, a pressure drop is produced from the second end 23 to the first end 21 of the outer tube, by virtue of the restriction provided by the inside tube 18. The pressure difference is generated between the ports 22 and 24. When a patient inhales from the first end 21 of the breath transmission tube, there is a pressure drop from the first end to the second end of the breath transmission tube, by virtue of the restriction provided by the inside tube. This produces a change in pressure across the ports 22 and 24 in the opposite direction from when the patient exhales. The change of pressure is sensed by a pressure sensor 26 connected by flexible tubing to the ports 22 and 24 of the outer breath transmission tube. The sensed pressure information can be used to control a ventilator 28 which produces ventilation air to the patient through flexible tubing 30. A humidifier 32 is connected in the ventilator air path between the ventilator and an adapter 34 at the downstream end of the breath transmission tube. The adapter is a Y-connection having inlet and outlet ports for alternately receiving ventilation air from the tubing 30 and cycling it to the patient or for transmitting exhaled air through flexible tubing 36 extending from the outlet port of the adapter 32 to the ventilator 28.

Figure 2:
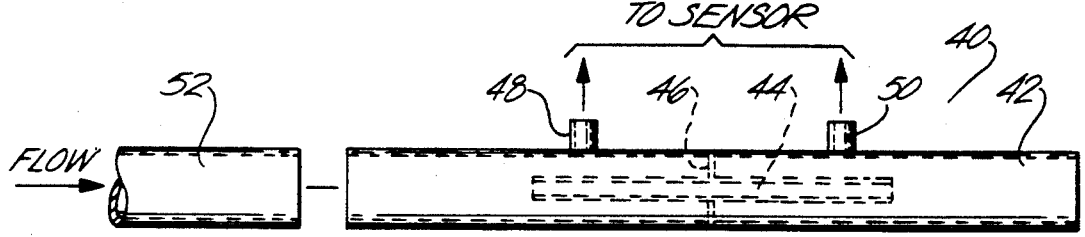
FIG. 2 is a schematic view showing a breath transmission tube and patient flow tube in a configuration known in the prior art.
Figure 3:
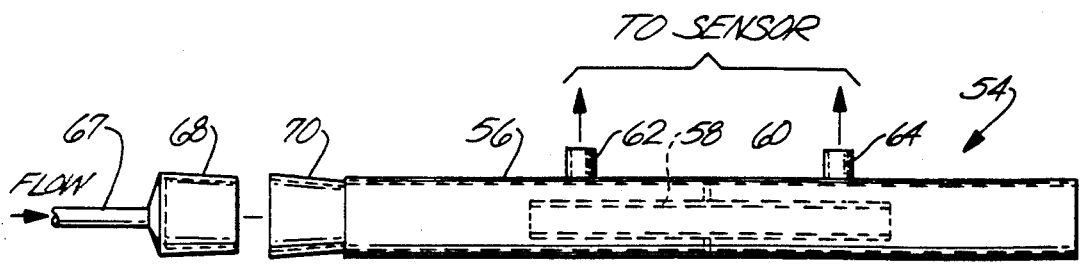
FIG. 3 is a schematic view showing an alternative breath transmission tube and patient flow tube and adapter used in the prior art.

The invention can be understood by first referring to the prior art flow heads shown in FIGS. 2 and 3. FIG. 2 schematically illustrates a flow head 40 which includes an elongated tubular outer passage 42, an elongated inside tube 44 of smaller diameter than the outer tubular passage, and an annular partition 46 that aligns the inside tube with the axis of the outer passage. As with the embodiment of FIG. 1, the outer passage 42 has a pair of axially spaced-apart ports 48 and 50 located on opposite sides of the partition, between the ends of the inside tube and the partition. As with the embodiment of FIG. 1, the restriction in the tubular outer passage 42 produces changes in pressure across the ports 48 and 50 in response to patient inhalation and exhalation through the passage. The patient inhales and exhales through a gas delivery tube 52 which, in this embodiment, has an inside diameter the same size as the outside diameter of the tubular outer passage 42. This type of large-diameter tube is used in spirometry or anesthesia. The ports 48 and 50 in the flow head are connected to a gas flow sensor, and a pressure drop across the head determines the flow through the sensor elements to produce an electrical output. If the gas flow is too high, the signal output either remains constant or increases very slowly. Thus, if it is desired to have a higher than recommended flow, a larger flow head must be used, but this can be easily accommodated by selecting a flow head having the appropriate dimensions.

Figure 4:
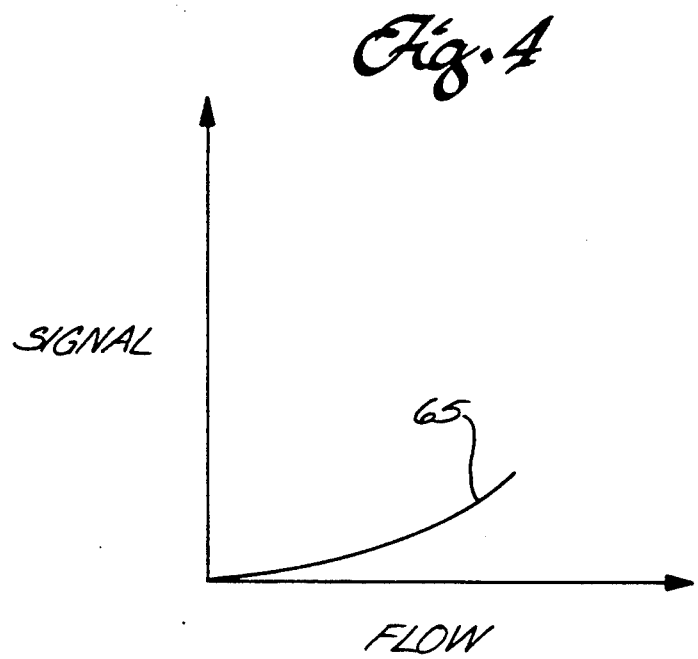
FIG. 4 is a graph showing a desired relationship between a voltage output signal and gas flow.
Figure 5:
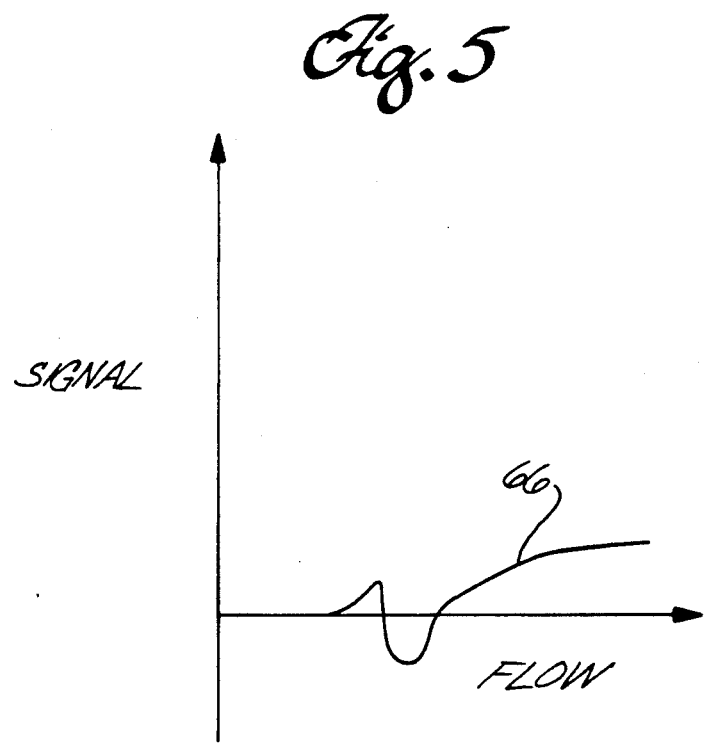
FIG. 5 is a graph showing an undesirable response of a voltage signal in relation to gas flow.

A serious problem arises, however, when an endotracheal tube connected to the flow head is relatively small in diameter compared to the inside tube of the flow head. This arrangement is shown in the prior art embodiment of FIG. 3, in which a flow head 54 includes an elongated tubular outer passage 56 containing an elongated inside tube 58 of smaller diameter than the outer tubular passage. The partition 60 aligns the inside tube 58 along the axis of the outer passage 56 of the flow tube. In this embodiment, ports 62 and 64 are located between the ends of the inside tube 58 and the partition 60. An endotracheal tube 67 of small-diameter connects to an end of the outer passage 56. Such an endotracheal tube is used in ventilator therapy, for example. This small-diameter endotracheal tube can be a standard 2.5 mm (approx. 0.10 inch) to 5 mm (approx. 0.20 inch) diameter tube for pediatric use. Larger adult-size endotracheal tubes are from about 6 mm to 9 mm in diameter. The endotracheal tube 67 has an adapter 68 of much larger diameter than the small-diameter tube 67. This adapter is coupled to the inside of an annular adapter 70 of matching configuration on the end of the flow passage 56. The adapters 68 and 70 are standard within the industry and have a slight angular taper of about one degree (the taper in the drawing is shown exaggerated to illustrate its angular inclination), so the endotracheal tube adapter 68 makes a tight fit inside the correspondingly tapered adapter 70 on the flow passage. In this embodiment, the small-diameter endotracheal tube 67, having a substantially smaller diameter than the inside tube 58, prevents laminar gas flow in the flow head. The gas can travel through the inside tube 58 of the flow head without producing a suitable pressure drop across the ports 62 and 64. The problem is so serious that, depending upon the flow, small changes in the flow can produce erratic signal changes which can suddenly go from positive to negative to positive. The gas flow-versus-voltage output desirably should be a smooth curve, similar to the curve 65 shown in FIG. 4; but instead, the gas flow-versus-voltage signal is erratic, such as the curve 66 shown in FIG. 5, which goes from positive to negative to positive. In addition, the signal output is very noisy.

The present invention is based on a recognition that the erratic signal conditions described above and illustrated in FIG. 5 occur when the flow head is connected to an endotracheal tube in which the inside diameter of the endotracheal tube is smaller than the diameter of the gas flow-restricting inside tube of the flow head. The inside diameter of the outer breath transmission passage is typically large to produce a low resistance path consistent with the desirable pressure drop, which is produced when the inside tube is also relatively large.

According to the present invention, the inside diameter of the flow head's inside tube is made equal to or very slightly less than the inside diameter of the endotracheal tube. Experiments have shown that, with the present invention, equilibrium gas flow conditions are established rapidly within the breath transmission passage, producing a very smooth pressure drop-versus-flow response, i.e., a highly stable measurement of the pressure flow drop across the head (across the output ports of the breath transmission passage). The experiments have shown that good results (smooth flow and a stable measurable pressure drop) are achieved when the inside diameter of the inside tube is equal to or within about 12% less than the diameter of the endotracheal tube. Experiments have also shown that only a very slight increase in the diameter of the flow head's inside tube, compared to the diameter of the endotracheal tube diameter, creates an unstable pressure drop across the flow head. This phenomenon also has been discovered to result essentially independently of the diameter of the endotracheal tube and independently of the length of the inside tube.

Figure 6:
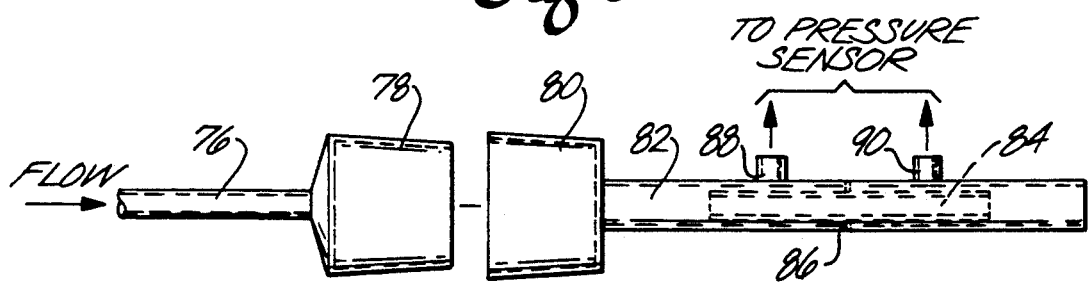
FIG. 6 is one embodiment of the invention showing a breath transmission tube connected to a small-diameter patient flow tube, for pediatric use.
Figure 7:
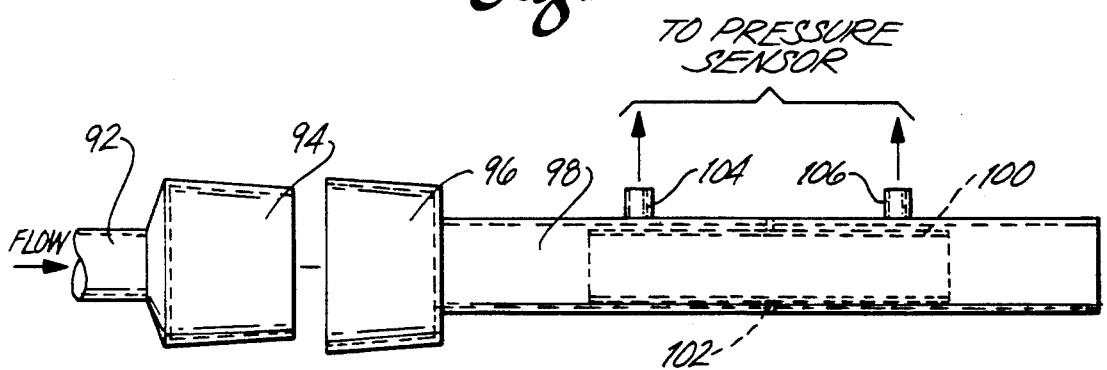
FIG. 7 is an alternative embodiment of the invention showing a breath transmission tube connected to a larger diameter patient flow tube for adult use.

FIGS. 6 and 7 illustrate different embodiments of the invention for use with endotracheal tubes of different sizes. FIG. 6 illustrates a small-diameter pediatric-size endotracheal tube 76 having a large-diameter tapered annular adapter 78 that makes a gas-tight sliding fit inside a correspondingly tapered annular adapter 80 on one end of the elongated tubular breath transmission passage 82. The inside tube 84 is positioned along the axis of the breath transmission passage and is held in place by the annular support 86. The outlet ports 88 and 90 communicate with a pressure sensor which can be used in this invention instead of a flow rate sensor having a source of bias gas. However, such a flow rate sensor also can be used, if desired.

In one embodiment, the inside diameter of the small-diameter endotracheal tube is 2.5 mm (approx. 0.100 inch). The inside diameter of the inside tube 84 of the breath transmission passage is also essentially the same diameter, i.e., 2.5 mm. Experiments have shown that the diameter of the inside tube 84 should not exceed the 2.5 mm inside diameter of the endotracheal tube. For instance, an inside tube having an inside diameter of 2.5 mm essentially equal to the 2.5 mm inside diameter of the endotracheal tube produces equilibrium rapidly and produces a highly smooth gas flow output. On the other hand, the same system used with a 2.7 mm (approx. 0.110 inch) inside tube in the breath transmission passage produces an undesired unstable pressure drop across the flow head. Stated another way, for a 2.5 mm diameter endotracheal tube, gas flow reaches equilibrium rapidly and produces a smooth gas flow output when the inside diameter of the endotracheal tube matches the inside diameter of the inner tube so that both are substantially the same in diameter. Even a slight increase in the diameter of the inside tube compared to the small-diameter endotracheal tube produces an unstable pressure drop across the head. On the other hand, if the inside diameter of the inside tube is made appreciably smaller than the diameter of the same endotracheal tube, gas flow through the inside tube is greatly restricted and produces too large a pressure drop across the outlet ports.

In one test for a 2.5 mm endotracheal tube, a pressure drop of 0.3 inch of water was produced across the flow head when the diameters of the endotracheal tube and the inside tube diameter were identical. However, when the inside tube diameter was reduced by 0.010 inch, gas flow resistance increased appreciably and the pressure drop across the head increased to 1.25 inches of water.

Another advantage of the invention is that the total gas volume within the flow head can be greatly reduced. For instance, the inside diameter of the breath transmission passage can be only slightly greater than the outside diameter of the inside tube. In the embodiment of FIG. 6, the breath transmission passage 82 can be only about 1/16 inch in diameter greater than the outside diameter of the inside tube 84. This greatly reduces the amount of dead space within the flow head. In the system shown in FIG. 6, for a 2.5 mm endotracheal tube, excluding the adapters (which have a dead volume), the dead volume of the head is only 0.22 cc.

FIG. 7 illustrates an alternative embodiment of the invention in which a flow head is coupled to a larger diameter adult endotracheal tube 92 which can be in the range of about 8.0 mm to 9.0 mm in inside diameter. In this embodiment, as with the embodiment of FIG. 6, the endotracheal tube is connected to an adapter 94 which makes a sliding fit in a correspondingly-shaped adapter 96 on a larger-diameter breath transmission passage 98. An inside tube 100 within the breath transmission passage 98 is retained in the tube by the annular support 102. The breath transmission passage has the outlet ports 104 and 106 on opposite sides of the partition for connection to a pressure sensor. Alternatively, the system is workable with a flow rate sensor having a source of bias gas. In one embodiment of FIG. 7, in which the inside diameter of the large-diameter endotracheal tube 92 is 8 mm (0.315 inch or approx. 5/16 inch), best results are achieved when the inside diameter of the inside tube 100 is almost equal to but slightly less than 8 mm. If the inside diameter of the inside tube is greater than the inside diameter of the endotracheal tube, poor results are achieved. When the two inside diameters are precisely the same, poor results also are obtained. On the other hand, if the inside diameter of the inside tube is about 1/32 inch (approx. one mm) less than the inside diameter of the endotracheal tube gas flow rate is smooth and a stable pressure drop is produced. Any greater difference (progressively smaller sizes of the inside tube compared to the endotracheal tube) produces poor results because the pressure drop within the flow head becomes too large. Best results are achieved when the inside diameter of the inside tube is not more than about 12% less than the diameter of the endotracheal tube. This embodiment of the invention, in which larger diameter endotracheal tubes are used, also can greatly reduce dead volume by the size of the inside tube very close to the size of the outer breath transmission passage, as shown in FIG. 7.

In one test for an 8 mm endotracheal tube, a pressure drop of four inches of water was produced across the flow head when the inside tube diameter was 7 mm. However, when the inside tube diameter was reduced to 6 mm, gas flow resistance increased greatly and the pressure drop across the flow head increased to ten inches of water.

Although the invention produces a slight increase in the overall resistance of the system the benefits of the new design are truly remarkable. First, the signal-to-noise ratio is higher while the pressure drop-versus-flow is a smooth curve. Secondly, the volume occupied by the head is the smallest available. Typically, the practice is to use one or more fine screens in the head to create a pressure drop, but these must be heated to prevent moisture from condensing, and they change the output even if dust particles become trapped. One recently introduced flowmeter uses a heated wire in the tube, but this approach has problems because of the following reasons. (1) The signal is small because the wire is short. (2) The wire is sensitive to changes in relative humidity during inhalation and changes in carbon dioxide during exhalation. (3) The wire becomes coated with foreign material during use, and the manufacturer suggests heating the wire to decompose the coating. (4) For the above the reasons the accuracy is not high, having a 7% to 10% error. (5) The smallest volume available is 1.4 cc. If in pediatric use the patient has a tidal volume of 5 cc and is rebreathing an exhaled volume of 1.4 cc, the carbon dioxide concentration in the blood increases, which is not a desirable condition. The smallest head using the improved design is 2.0 mm in diameter. It is much less expensive to manufacture and is easily cleaned.

The pressure drop was measured across the endotracheal tube, across the flow head alone, and across the combined endotracheal tube and flow head. All measurements were made at the same gas flow. The following table shows the results of this experimental data.

| ET Tube Size (mm) | ΔP across ET Tube (in. $H_2O$) | ΔP across Flow Head (in. $H_2O$) | ΔP across ET Tube and Flow Head (in. $H_2O$) |
|---|---|---|---|
| 8.0 | 10.75 | 6.0 | 13.0 |
| 9.0 | 7.75 | 3.25 | 9.25 |

One would expect that the fourth column would equal the sum of columns two and three, but that is not the case. The conclusion from the experimental results is that the flow head resistance does not add much resistance to the endotracheal tube resistance. Thus, the patient does not expend that much more effort to obtain the benefits of accurate flow measurements at the patient gas flow tube. The new pressure sensors which are now available can measure full scale at four inches of water. While not as sensitive as flow sensors, they have the advantage of simplicity without the bias flow and other components used in a flow sensor. The new flow head of this invention is easily matched to the new pressure sensor, although the previous flow heads (such as those shown in my previous U.S. patents, have a small pressure drop across them (approx. 0.2 inches of water) so are matched to the flow sensor. (My previous U.S. patents related to such gas flow rate sensors are U.S. Pat. Nos. 4,259,968; 3,949,739; and 3,235,752.)

Figure 8:
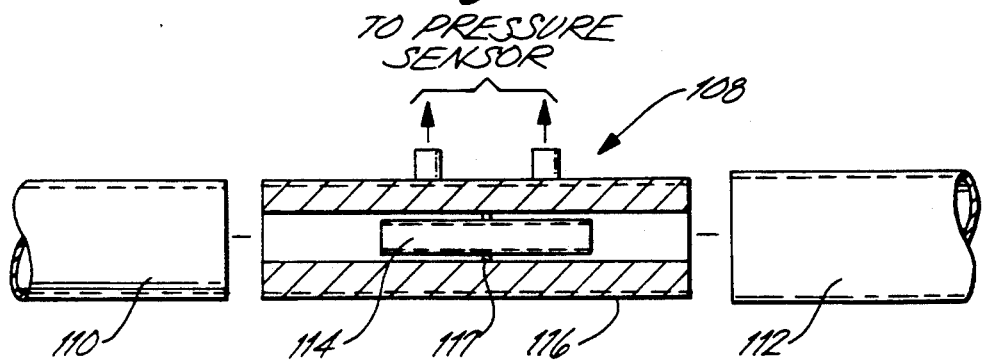
FIG. 8 is an embodiment of the invention showing a breath transmission tube corrected to a patient flow tube for adult spirometry for example.

FIG. 8 illustrates a flow head of this invention which may be used in adult anesthesia or spirometry. The gas delivery tubes 110 and 112 used in adult anesthesia or spirometry are typically 22 mm in inside diameter. The inside diameter of the center tube 114 of the head is approximately 8 mm to provide a pressure drop across the pressure sensor. Thus, one would expect a noise problem to develop if the gas flow tubes at the upstream and downstream ends of the flow head are each 22 mm in diameter, if the inside tube is 7 mm in diameter, and if the outer breath transmission tube 116 is about 9 mm in diameter. During use, gas flowing from the 9 mm diameter to the 22 mm diameter is a sudden large change in diameter, but surprisingly, not much noise is generated. However, if gas flowing in the 7 mm inside tube 114 went to a 12 mm diameter breath transmission passage and then to the 22 mm anesthesia tube 112 at the downstream end of the flow head, there would be a much greater amount of noise. An important feature in noise reduction is the small annular ring between the inside tube and the breath transmission passage. The breath transmission passage 116 has an annular ring 117 between it and the inside tube 114. Thus, it is now possible to use the endotracheal tubes with the new flow heads, as well as standard anesthesia or spirometry tubing with the new flow head.

What is claimed is:

1. For use in a pulmonary gas flow system having a flow head for measuring gas flow in the pulmonary system, and a patient gas delivery tube connected to an upstream end of the flow head, in which the flow head includes an elongated open-ended tubular breath transmission passage, an elongated open-ended inside tube mounted axially inside the breath transmission passage to provide a constriction to gas flow in the passage, a pair of axially spaced-apart outlet ports in the side of the breath transmission passage arranged to produce a pressure drop across the outlet ports in response to constricted gas flow in the breath transmission passage, and a patient gas delivery tube coupled to the upstream end of the breath transmission passage for directing the flow of patient gas through the passage the improvement in which the inside tube has an inside tube inside diameter and an inside tube outside diameter and the patient gas delivery tube has a delivery tube inside diameter which is substantially the same size as the inside tube inside diameter sufficient to produce a smooth flow of gas through the passage with a stable measured gas pressure drop across the outlet ports of the flow head.

2. The improvement according to claim 1, in which the inside tube inside diameter is within a tolerance range of plus zero to minus about 12% compared to the delivery tube inside diameter.

3. The improvement according to claim 2 in which the patient gas delivery tube is an endotracheal tube for pediatric and adult use having an inside diameter in the range from about 2.5 mm to about 9 mm.

4. The improvement according to claim 1 in which the breath transmission passage has a passage inside diameter in the vicinity of the inside tube which is not more than about 5% greater than the inside tube outside diameter so as to substantially reduce dead space within the pulmonary system.

5. The improvement according to claim 1 in which the pulmonary system includes a ventilator and bi-directional gas flow tubing extending between the ventilator and a downstream end of the breath transmission passage.

6. The improvement according to claim 1 in which the patient gas delivery tube is for pediatric use and is an endotracheal tube having an inside diameter from about 2.5 mm to about 5 and in which the inside tube inside diameter is substantially equal to the inside diameter of the endotracheal tube.

7. The improvement according to claim 1 in which the patient gas delivery tube is for adult use as an endotracheal tube having an inside diameter in the range from about 8 mm to about 9 mm and the inside tube inside diameter is not more than about 1/16 inch less than the delivery tube inside diameter.

8. The improvement according to claim 1 in which the gas delivery tube is an endotracheal tube having an inside diameter from about 2.5 mm to about 9 mm and in which the inside tube inside diameter varies from about zero to about one mm less than the inside diameter of the endotracheal tube.

9. For use in a pulmonary gas flow system having a flow head for measuring gas flow in the pulmonary system, and a patient gas delivery tube connected to an upstream end of the flow head, in which the flow head includes an elongated open-ended tubular breath transmission passage, an elongated open-ended inside tube mounted axially inside the breath transmission passage to provide a constriction to gas flow in the passage, a pair of axially spaced-apart outlet ports in the side of the breath transmission passage arranged to produce a pressure drop across the outlet ports in response to constricted gas flow in the breath transmission passage, and a patient gas delivery tube coupled to the upstream end of the breath transmission for directing the flow of patient gas through the passage, in which the gas delivery tube has an inside diameter sufficient for use for adult anesthesia or spirometry and substantially greater in diameter than the inside tube of the breath transmission passage, the improvement in which an annular space between the inside tube having an inside tube inside diameter and the breath transmission passage having an inside diameter comprises an elongated.

10. The improvement according to claim 9 in which the gas delivery tube has a delivery tube inside diameter which is more than twice the inside tube inside diameter.

* * * * *

UNITED STATES PATENT AND TRADEMARK OFFICE
CERTIFICATE OF CORRECTION

PATENT NO. : 5,313,955
DATED : May 24, 1994
INVENTOR(S) : Jerome A. Rodder

It is certified that error appears in the above-indentified patent and that said Letters Patent is hereby corrected as shown below:

Column 7, line 31, before "reasons" delete "the".

Column 7, line 67, change "0.2 inches" to -- 0.2 inch --.

Column 9, line 7, after "5" insert -- mm --.

Column 10, line 19, after "elongated" insert -- annular ring occupying a dead volume in the annular space between the inside tube and the inside diameter of the breath transmission passage so as to minimize the dead volume within the flow head --.

Signed and Sealed this

Eighteenth Day of April, 1995

Attest:

BRUCE LEHMAN

Attesting Officer

Commissioner of Patents and Trademarks